United States Patent [19]

Deppert et al.

[11] Patent Number: 5,087,733

[45] Date of Patent: Feb. 11, 1992

[54] SULFUR CONTAINING QUATERNARY AMMONIUM SALTS AS HAIR CONDITIONING AGENTS

[75] Inventors: Thomas M. Deppert, Waterbury; Janusz Z. Jachowicz, Bethel; Bryan P. Murphy, Monroe, all of Conn.

[73] Assignee: Clairol, Inc., New York, N.Y.

[21] Appl. No.: 562,307

[22] Filed: Aug. 3, 1990

[51] Int. Cl.$^5$ ............................................ C07C 321/14
[52] U.S. Cl. .................................... 560/147; 564/227; 564/243; 564/225; 564/291; 564/295; 424/70; 424/72
[58] Field of Search ............... 564/227, 243, 225, 291, 564/295; 560/147

[56] References Cited

U.S. PATENT DOCUMENTS

| | | | |
|---|---|---|---|
| 2,125,901 | 8/1938 | Evans et al. | 564/291 |
| 2,777,858 | 1/1957 | Riehen et al. | 564/295 |
| 3,510,248 | 5/1970 | Thielan et al. | 8/116.2 |
| 3,732,310 | 5/1973 | Huber | 64/291 |
| 3,834,867 | 9/1974 | Matter et al. | 8/115.5 |
| 4,052,440 | 10/1977 | Gladstone et al. | 560/147 |
| 4,067,901 | 1/1978 | Gladstone et al. | 560/147 |
| 4,299,817 | 11/1981 | Hannen et al. | 424/70 |

FOREIGN PATENT DOCUMENTS

| | | | |
|---|---|---|---|
| 1164163 | 3/1953 | France | 564/295 |
| 641157 | 5/1962 | United Kingdom | 564/291 |

OTHER PUBLICATIONS

A. C. Lunn and R. E. Evans, The Electrostatic Properties of Human Hair, J. Soc. Cosmet. Chem., 28, 549 (1977).

*Primary Examiner*—James H. Reamer

[57] ABSTRACT

Processes for conditioning human hair by treatment with selected sulfur containing quaternary ammonium compounds, compositions useful for such processes and novel quaternary compounds useful in the processes.

8 Claims, No Drawings

SULFUR CONTAINING QUATERNARY AMMONIUM SALTS AS HAIR CONDITIONING AGENTS

FIELD OF THE INVENTION

This invention is in the field of human hair conditioners to make such hair more manageable.

The invention, which utilizes novel compounds, relates to a process for conditioning human hair especially, although not necessarily after waving. It relates also to compositions containing the novel compounds. More particularly, it relates to certain quaternary ammonium salts with at least one long chain substituent attached to the nitrogen of the quaternary center, and to the utility of such salts as hair conditioners.

BACKGROUND OF THE INVENTION

It is known that when certain long chain alkyl quaternary ammonium salts are deposited on human hair, they improve combability i.e. the relative ease with which hair can be combed, by imparting a certain lubricity to the hair as well as by providing an antistatic effect. Both of these effects combine to make the hair easier to manage so that the desired appearance of the hair can be more readily achieved. Compositions having these properties are called "hair conditioners". See, for example, A. C. Lunn and R. E. Evans, The Electrostatic Properties of Human Hair, J. Soc. Cosmet. Chem., 28, 549 (1977).

These hair conditioners appear to function because they are cationic and are easily absorbed on the anionic surface of the human hair. However the conditioning effect is usually short lived because the conditioners wash out of the hair and are substantially eliminated after only a few washings.

The art has made many efforts to overcome the problem and provide durable hair conditioners which will stay on the hair despite hair washings.

Hannen et al in U.S. Pat. No. 4,299,817 describe an aqueous composition for setting hair which contains as the active ingredient, a polyelectrolyte complex which is the ionic reaction product of one or more polycationic polymers and one or more polyanionic polymers.

Quaternary ammonium salts are also known for other purposes.

For example, U.S. Pat. No. 3,510,248 to Thielan et al discloses certain chloro quanternary compounds for softening cellulosic materials e.g. cotton textile fibers.

Matter et al in U.S. Pat. No. 3,844,867 describe the use cationic quaternary ammonium halides substituted with an alkylene halide group or an alkyl halide group interrupted with a phenylene group for improving the affinity of anionic dyes to textiles such as nylon.

Despite major efforts, however, the art has not yet provided durable hair conditioners which will continue their desirable effects in human hair through several shampoos.

THE INVENTION

It has now been discovered that certain novel cationic, quaternary ammonium salts can be employed as hair conditioners which will continue to provide their beneficial conditioning effects through eight or more shampoos. This invention is concerned with such compounds, hair conditioning compositions containing one or more of these compounds and methods of employing them to improve the combability of hair.

The novel compounds useful in this invention are sulfhydryl, disulfhydryl, dithio, isothiuronium or diisothiuronium quaternary ammonium salts, suitably halides, having at least one long chain alkyl or modified alkyl group. They may be represented by the formulas:

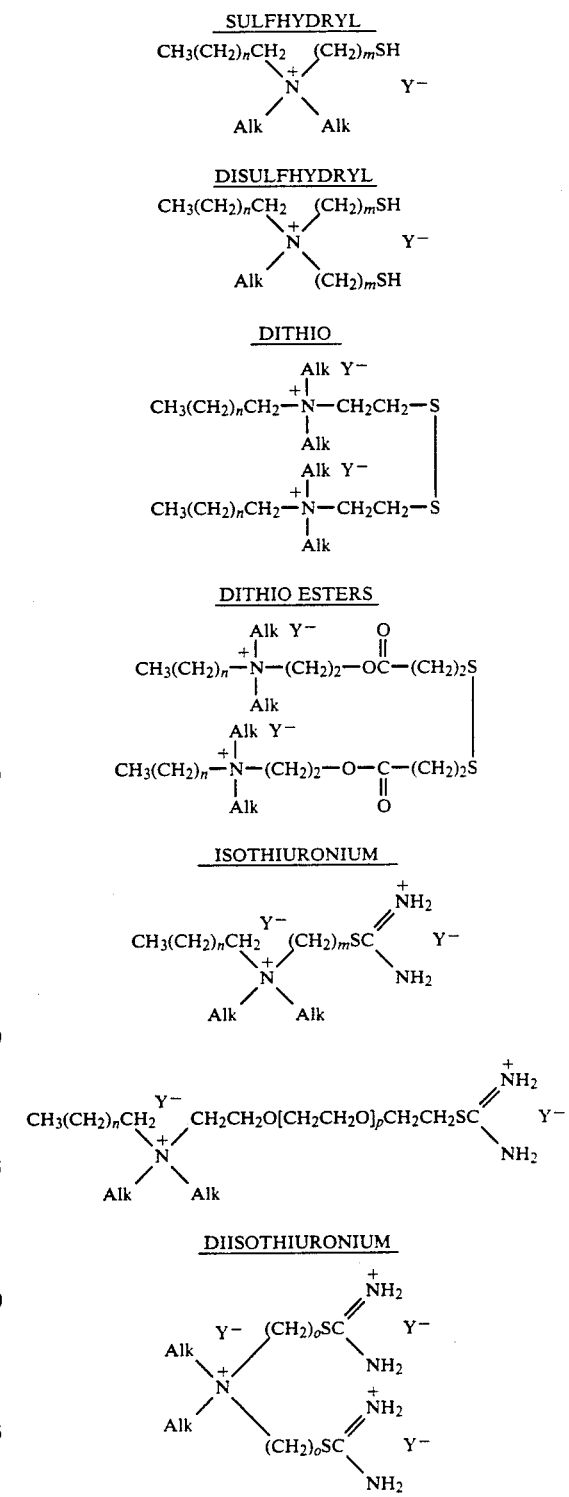

-continued

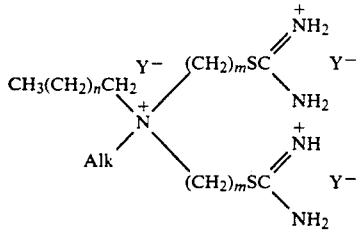

wherein

Alk is an alkyl group containing from about 1 to about 4 carbon atoms

Y is an anion n is an integer with a value of from about 10 to 24 m is an integer with a value of from about 1 to about 4 o is an integer with a value of from about 8 to about 11 p is an integer with a value of from about 0 to about 20 provided that, in compounds with only one n integer, the total number of carbon atoms in the cation is not greater than 28, and in compounds with two n integers, the total number of carbon atoms in the cation is not more than about 52, and further compounds in which one or both long chain alkyl groups is interrupted with a phenylene group so that the structure of the interrupted group can be represented by the formulas:

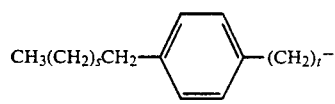

wherein s is an integer of from about 8 to about 17 and t is an integer from about 1 to about 5.

It should be noted that in the compounds of the invention with pairs of substituents, e.g., two alkyl groups or two long chain alkyl groups, the members of each pair do not need to be identical, although usually they will be.

The compounds of the invention can be prepared by any of a number of procedures known to those skilled in the art.

For example, isothiuronium and diisothiuronium salts can be prepared by reaction of the corresponding bromides and thiourea in a reaction inert, polar, organic solvent such as ethanol at a temperature of from about 50° to about 80° C. for from about 4 to about 6 hours. The methods for the preparation of the monobromides and the necessary starting compounds are known. The dibromides can be prepared from the corresponding dialcohols by reaction with a molar excess of phosphrous tribromide in an organic hydrocarbon solvent such as benzene.

The mono-and disulfhydryl compounds are also prepared from the corresponding bromides by reaction with sodium hydrosulfide in a reaction inert, polar, organic solvent such as ethanol at a temperature of from about 25° C. to 40° C. for from about 20 to about 50 hours.

The following equations illustrate, by way of example, methods for preparing the dithio compounds:

Dithio esters

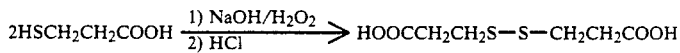

A

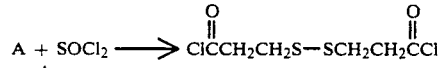

B

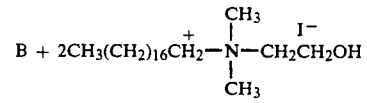

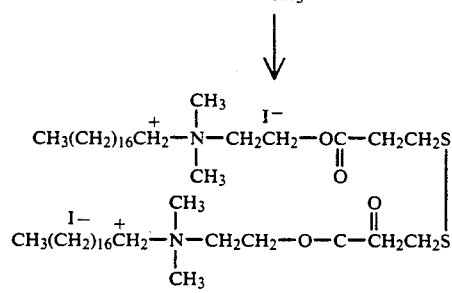

Dithio compounds

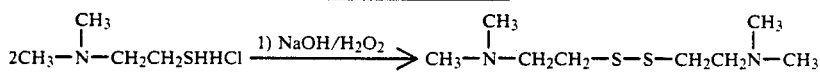

C

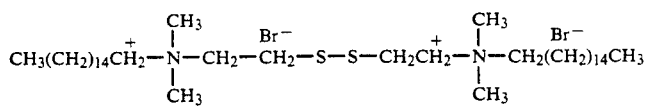

The following non-limiting examples illustrate these methods of preparing compounds of the invention.

EXAMPLE I

General Procedure For Preparation of Isothiuronium Salts

Dimenthyl-(2- bromoethyl)hexadecyl ammonium bromide (9.14g, 0.020 mole) and thiourea (1.52g, 0.020 mole) were dissolved in pure ethanol and allowed to reflux for 4-6 hours. Upon cooling a precipitate formed. This white precipitate was filtered and recrystallized from ethanol. Dimethyl-(2-isothiuranyl)ethyl hexadecyl ammonium dibromide was obtained in a 71% (7.54g) yield. $^1$HNMR $D_2O_2$) 0.878(t, 3H), 1.27 (broad s, 26H), 1.75 (m, 2H), 3.18 (s,6H), 3.40 (m, 2H), 3.66 (broad s, 4H).

calc: .%C 47.27; %H 8.89; %N 7.88; %S 6.04; %Br 29.95;

found: %C 47.09; %H 8.85; %N 7.87; %S 6.14; %Br 29.73;

The IR analysis also agreed with the proposed structure.

EXAMPLE II

General Procedure For Preparation of Disulfide Diesters

A. Dithio Diacid

Mercaptopropionic acid (26.5 g 0.259 mole) was slowly added to a 250 mL aqueous solution of sodium hydroxide (50 g, 1.25 mole) and hydrogen peroxide [16.25 mL, 30% (wt./vol.), 0.125 mole]and was allowed to react for 3h. The disulfide diacid salt was precipitated with conc. HCl. The white solid was filtered and dried. The disulfide diacid was isolated in a 50% (13.0 g) yield and used in the next step without further purification. m.p. 155°-158° C.; $^1$HNMR (DMSO- d6) 2.60 (t,4H), 2.89 (t, 4H). IR analysis agreed with the proposed structure.

B. Dithio Diester

The above acid (2.1 g, 0.010 mole) was dissolved in 50 mL of thionyl chloride ($SOCl_2$) as both reactant and solvent. The mixture was allowed to reflux for 4h. The excess $SOCl_2$ was then removed in vacuo and the residue was dissolved in a minimal amount of anhydrous $CH_2Cl_2$. Dimethyl-(2-hydroxyethyl)octadecyl ammonium iodide (9.40 g, 0.020 mole) and crosslinked-polyvinylpyridine (2.1 g,0.020 mole) were then added and the mixture was allowed to react overnight at room temperature under a nitrogen atmosphere. The PVP was then filtered off, the solvent was removed, and the resulting solid was recrystallized from ethyl acetate. The disulfide diester diammonium salt was obtained in a 43% (4.80g) yield. $^1$HNMR ($CDCl_3$) 0.86 (t,6H), 1.26-1.50 (m, 64H), 2.9 (m, 4H), 3.0 (m,4H), 3.36-3.60 (m, 20H), 4.14 (broad s, 4H). IR analysis agreed with the proposed structure.

EXAMPLE III

General Procedure For Preparation of Dithio Compounds

III. Synthesis of Dithio Compounds

The disulfide diamine precursoer was synthesized as described in II A (above) from 2-dimethylaminoethanethiol hydrochloride [17.16g RSH.HCl, 0.121 mole; 7.87 mL $H_2O_2$ (30% wt/vol), 0.0606 mole; 29.08 g NaOH in 121.1 mL $H_2O$]. The disulfide diamine was extracted from the water with diethyl ether. The resulting oil was dried to yield 8.47g (67% yield) of the desired product. $^1$H NMR ($CDCl_3$) 2.10 (m,12H), 2.45 (m,4H), 2.65 (m, 4H). This oil (2.1g, 0.010 mole) was dissolved in acetonitrile and 7.2g (0.020 mole) of hexadecylbromide was added and the mixture was allowed to reflux for 4h. The white precipitate was recrystallized from acetonitrile to yield 4.0g(50%) of the desired disulfide diammonium salt. $^1$H NMR ($CDCl_3$) 0.879 (t, 6H), 1.25-1.36 (m, 52H), 1.75 (m, 4H), 3.45 (s, 12H), 3.60 (m, 8H), 4.06 (t, 4H).

EXAMPLE IV

General Procedure For Preparation of Sulfhydryl Compounds

Dimethyl-(2-bromoethyl)hexadecyl ammonium bromide (4.57 g, 0.010 mole) was dissolved in pure ethanol and added dropwise to a solution of sodium hydrosulfide (0.92g, 0.010 mole in ethanol) and was allowed to react for 48h at room temperature. The ethanol was removed and the white solid was recrystallized from ethyl acetate to yield 3.27 g (80%) of the desired compound. $^1$HNMR ($CDCl_3$) 0.880 (t, 3H), 1.25-1.40 (m, 26H), 1.84 (m, 2H), 2.81 (s, 6H), 3.00 (t, 2H), 3.43 (m, 4H).

Utilizing these general procedures, the compounds listed below were prepared. They were all identified by elemental analysis, $^1$HNMR and IR. They are all novel and are the presently preferred compounds of the invention.

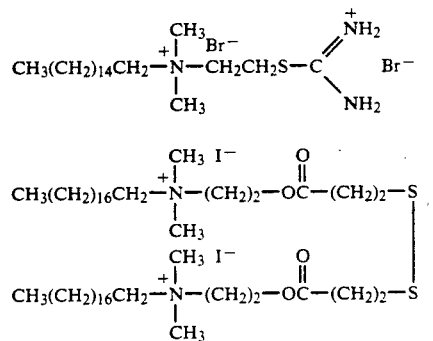

-continued

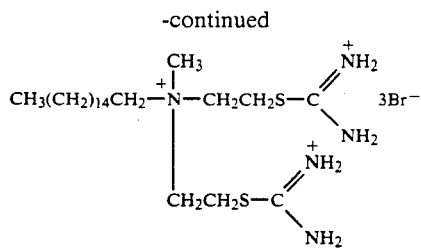

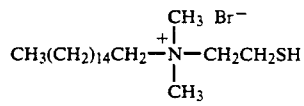

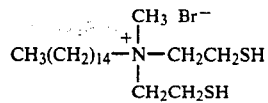

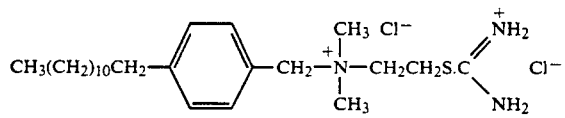

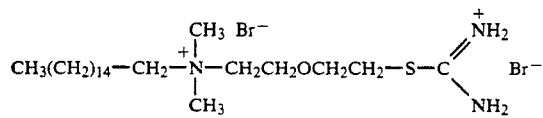

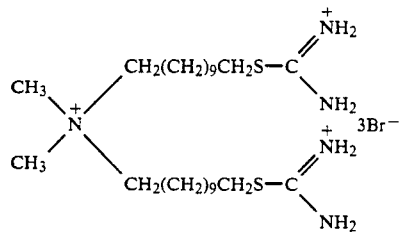

The compounds listed in Table I are all prepared as described above and are useful in the practice of this invention.

TABLE I $$R_2-\overset{R_1^+}{\underset{R_3}{N}}-R_4\ Y^-$$

| R1 | R2 | R3 | R4 | Y |
|---|---|---|---|---|
| CH3 | CH2CH2SC(=NH2)NH2 | CH3(CH2)10CH2 | CH2CH2SC(=NH2)NH2 | 3Br |
| CH3 | CH3 | CH3(CH2)12CH2 | (CH2)3SH | Cl |
| CH3CH2 | CH2CH2SH | CH3(CH2)8CH2 | CH2CH2SH | Br |
| CH3CH2CH2 | CH3CH2CH2 | CH3(CH2)10CH2 | CH2CH2SH | Cl |
| CH3 | CH3 | CH3(CH2)12CH2 | CH2CH2SC(=NH2)NH2 | Br |

The hair conditioning agents of this invention have a number of advantages compared to hair conditioners of the prior art. Their principal advantage is that they are very durable and will remain in the hair as effective conditioners even after several shampoos, e.g. four to eight or more. Their durability is attributable to at least two factors. One is that they form ionic bonds with the hair. The other is that they may form covalent bonds with the hair. Additionally, under certain conditions they may be insolubilized on or near the surface of the hair and provide a conditioning effect.

As is known, the keratin of human hair carries an anionic charge. The hair conditioners of the invention are cationic and are electrostatically attracted and bound to the hair. Human hair, especially after waving with reducing agents such as thioglycolic acid has a number of free mercaptan groups formed by reductive cleavage of the disulfide bonds of cystine. The compounds of this invention react with the free mercaptan groups to form covalent bonds which binds the conditioner to the hair. The presence of the long chain alkyl group in the moiety chemically joined with the hair improves the lubricity. As a result of these two reactions, the combability of the hair is greatly improved.

The reaction for the formation of covalent bonds for certain of the compounds of the invention is illustrated below wherein R represents the long chain substituent and K represents keratin protein.

Reduction

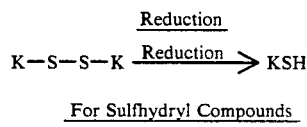

A

For Sulfhydryl Compounds

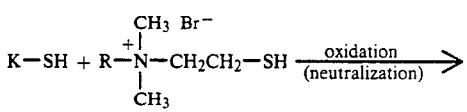

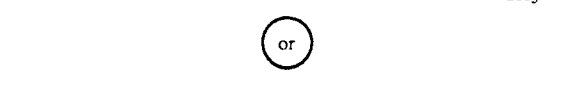

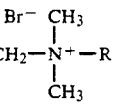

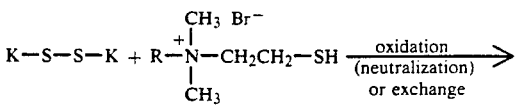

-continued
Reduction

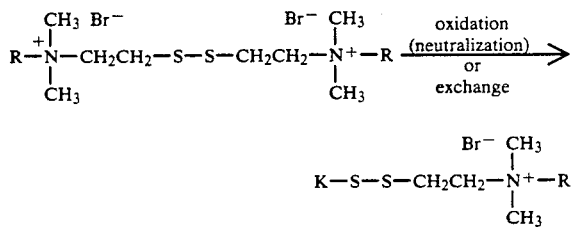

For Dithio Compounds

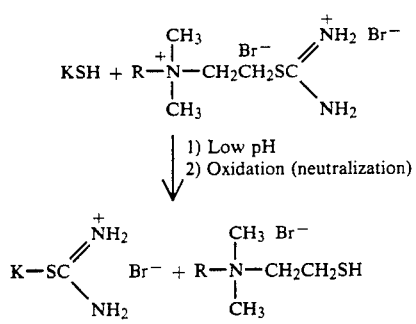

For Monoisothiuronium Compounds at Low pH

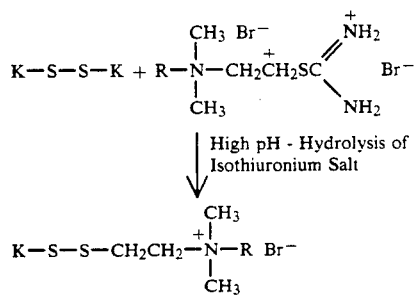

For Monoisothiuronium Salts At High pH

K—S—S—K + R—N(CH$_3$)(CH$_3$)—CH$_2$CH$_2$SC(=NH$_2^+$)(NH$_2$) Br$^-$  Br$^-$

High pH - Hydrolysis of Isothiuronium Salt

K—S—S—CH$_2$CH$_2$—N$^+$(CH$_3$)(CH$_3$)—R  Br$^-$

One of the advantages of the sulfhydryl, disulfhydryl and isothiuronium compounds of this invention is that they can be, although they need not be, incorporated in the waving lotions utilized in the procedure of waving hair and will subsequently react during the oxidation or neutralization procedure. They can also react with untreated hair in aqueous solutions at high pH. Accordingly, the process of the invention is not limited to utilization with the waving procedure.

The disulfhydryl, dithiols and diisothiuronium hair conditioners of the invention are preferred because, as will be apparent from their structure, each molecule is capable of forming two covalent bonds with the sulfhydryl radicals of the hair. Thus, they are more effective than the monofunctional compounds at reducing wet combing work.

It should be noted that the hydrolyzed isothiuronium compounds are effective in increasing the viscosity of the conditioning solutions. The maximum viscosity was observed to be dependent upon concentration, pH and the structure of the isothiuronium salt. This property increases the ease of formulation by decreasing the need for thickening agents.

The products of this invention are especially useful after waving with ammonium thioglycolate or with an inorganic reducing agent such as sodium bisulfite. However, they may also be employed with untreated or virgin hair, dyed hair, relaxed hair and bleached hair. In all cases they reduce the combing work as determined by the method of Garcia and Diaz described in J. Soc. Cosmet. Chem. 27, 379–398 (September 1976).

Combability can be defined as the subjective perception of the relative ease or difficulty with which human hair can be combed. It depends on the magnitude of the fluctuations of the forces that oppose combing.

As discussed at page 379 by Garcia and Diaz in the cited publication, which is incorporated herein by reference:

Combability is an important attribute, which is always considered when judging the "condition" of human hair. Improved combability is perceived as the hair being in better condition. Another concept closely associated with combability is that of manageability. Still another factor related to combability is that of the mechanical damage, which is done to hair with the combing process, which is accelerated if the hair is hard to comb or to untangle. It follows that combability, due to its close connection with other desirable hair qualities, is a very important factor in judging the performance of many hair care products.

The hair conditioners of this invention will normally be contacted with the hair to be treated from the waving lotion or from water or water/alcohol solutions containing from about 0.1% to about 10% by weight, based on the total weight of the composition, of at least one of the active agents. Preferred solutions will contain from about 0.5% to 5% of at least one conditioner. Aqueous solutions are preferred, but the compositions may contain up to about 30% by weight of water miscible lower alkanol, preferably ethanol or isopropanol as well as benzyl alcohol to assist in solubilizing the conditioner or other components of the composition which may be present. The additional excipients include, for example coloring agents, fragrances, surfactants, buffers, preservatives, viscosity enhancers, gelling agents, silicones or other emulsifying agents, and other common adjuvants well known to those skilled in the art.

The compositions may be provided as foams, gels, aerosols or other standard forms normally employed with such products. These may be produced by procedures well known to the skilled artisan. The contact time is from about 5 to about 30 minutes.

A number of tests have been conducted with the conditioners of this invention to determine their efficiency as hair conditioning agents. These test were conducted on untreated, reduced and dyed hair at various pH values. The results are shown in Table II.

For untreated hair, each experiment was performed on a 6 inch 2 g tress of virgin brown hair. Measurements of wet combing work were obtained on an Instron Model 1110 with a cross-head speed of 10 cm/min using the procedure cited above. The results reported in the table are the average of the measurements obtained for two tresses.

In the first set of tests on untreated hair, the hair was treated with a 1% aqueous solution of the selected conditioner for 30 minutes at room temperatures and then rinsed with warm tap water for 1 minute. In the subsequent shampooing, the hair was lathered with 0.5 g of a commercial shampoo for 30 seconds followed by rinsing under warm tap water for 30 seconds.

For waving, the hair was treated with ammonium thioglycolate (6% adjusted to pH 9) for 10 minutes at room temperature and rinsed with tap water for 1 minute. Then it was treated with 10 ml of an aqueous 1% solution of the selected conditioner for 30 minutes at room temperature prior to neutralization, i.e. oxidation with 10 ml. of 3% H for 8 minutes at room temperature. It was then shampooed as described above.

The tests were then expanded to include dyed hair. After dyeing with a commercial dye, the hair is treated with 10 ml of 1% aqueous solution of the selected conditioner for 30 min. at room temperature. They were then rinsed with warm tap water for 1 min. and shampooed as above.

The conditioners tested were:

A: Dimethyl - 2-(isothiuranylethyl)-hexadecyl ammonium dibromide

B: Methyl - di - [(2- isothiuranyl)]- hexadecyl ammonium dibromide

TABLE II

| | | Wet Combing Work | |
| | | Wet Combing Work (g*cm) | |
| Treatment | pH of the Treatment | After Treatment | After 4 Shampoos | After 8 Shampoos |
|---|---|---|---|---|
| Virgin Hair | | | | |
| Untreated (virgin) | 5.3 | 952 | 3006 | 2941 |
| | 10.7 | 1114 | 1855 | 3270 |
| Stearalkonium Chloride | 5.3 | 715 | 1078 | 1704 |
| | 10.7 | 888 | 640 | 1504 |
| Conditioner A | 5.3 | 719 | 594 | 1108 |
| | 10.7 | 1004 | 340 | 708 |
| Conditioner B | 5.3 | 552 | 630 | 1074 |
| | 10.7 | 303 | 207 | 582 |
| Reduced Hair | | | | |
| Untreated (reduced) | 5.3 | 1515 | 3470 | 3846 |
| | 10.7 | 1005 | 3625 | 4262 |
| Stearalkonium Chloride | 5.3 | 1066 | 622 | 973 |
| | 10.7 | 454 | 664 | 991 |
| Conditioner A | 5.3 | 2360 | 975 | 1645 |
| | 10.7 | 1804 | 1587 | 1944 |
| Conditioner B | 5.3 | 264 | 523 | 616 |
| | 10.7 | 278 | 904 | 1502 |
| Dyed Hair | | | | |
| Untreated (Dyed) | 10.7 | 5956 | 5721 | 4439 |
| Stearalkonium Chloride | 10.7 | 2200 | 2654 | 3234 |
| Conditioner A | 10.7 | 1960 | 4982 | 4416 |
| Conditioner B | 10.7 | 1128 | 2748 | 4538 |

Compound B was then tested as described above, but with only 5 minutes of treatment instead of 30 minutes. The results were compared with those achieved with stearalkanium chloride a widely employed hair conditioning agent. The results are shown in Table III

TABLE III

| | | Wet Combing Work (g*cm) | |
| | pH of the Treatment | After Treatment | After 4 Shampoos | After 8 Shampoos |
|---|---|---|---|---|
| Virgin Hair | | | | |
| Untreated (Virgin) | pH 10.7 | 966 | 3081 | 3803 |
| Stearalkonium chloride | pH 10.7 | 520 | 626 | 1821 |
| Conditioner B | pH 10.7 | 296 | 508 | 1125 |
| Reduced Hair | | | | |
| Untreated (Reduced) | pH 5.3 | 1404 | 3548 | 4431 |
| Stearalkonium chloride | pH 5.3 | 928 | 461 | 912 |
| Conditioner B | pH 5.3 | 404 | 648 | 639 |

It will be seen that the compound of the invention is very effective in reducing wet combing work.

It will be seen that the compound of the invention is very effective in reducing wet combing work.

Table IV records the results of tests with a variety of conditioners as additives in waving lotions. For the reduction, the hair was treated with 10 ml of a aqueous mixture that contained a reducing agent, ammonium thioglycolate, 10% adjusted to pH 9.2, (TGA) or glycerol monothioglycolate 20% adjusted to pH 9.2, (GMT) and 5% of the selected conditioner for 30 minutes at room temperature. The hair was then rinsed with warm tap water for 1 minute, and neutralized with 3% peroxide for 8 minutes. Subsequent shampooing were performed as described above.

TABLE IV

| | Wet Combing Work (g*cm) | | | |
| Additives | After Treatment | After 4 Shampoos | After 8 Shampoos | Liquid Retention (%) |
|---|---|---|---|---|
| Untreated (TGA reduced) | 617 | 1735 | 3043 | 46 |
| Untreated (GMT reduced) | 2542 | 6047 | — | — |
| 5% Stearalkonium Chloride | 652 | 395 | 2748 | 50 |
| 5% Dithio | 511 | 4850 | — | 37 |
| 5% Dithio Diester* | 117 | 3210 | — | — |
| 5% Conditioner A | 289 | 360 | 1784 | 54 |
| 5% Conditioner B | 231 | 880 | 1950 | 49 |
| 5% Sulfhydryl | 144 | 2813 | — | 48 |
| 5% Disulfhydryl | 383 | 412 | 1560 | 45 |
| 1% Kerasol** | 780 | 1807 | 2055 | — |
| 1% Croquat WKP** | 698 | 2368 | 5747 | — |

*The Dithio diester was added to 20% glycerol monothioglycolate (GMT).
**Commercially available hair conditioning agents Conditioners A and B are defined above. The formulas for the other compounds of Table IV are as follows:

Dithio diester

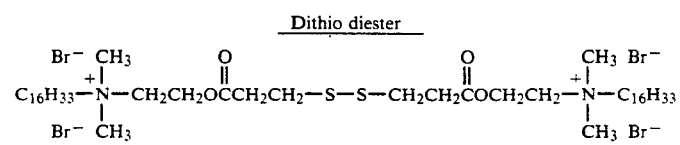

Dithio

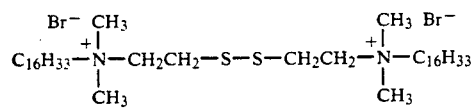

Sulfhydryl

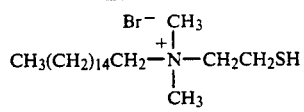

Disulfhydryl

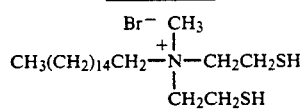

Conclusions based on Table II, Table III and Table IV

The results presented in Table II show that although the conditioners reduce the wet combing work at both pH values, they work best on untreated hair from high pH solutions, while on reduced hair they work best from low pH solutions. This conditioning effect was even more pronounced in the case of untreated or reduced hair treated with Conditioner B. As expected in the case hair treated with oxidative dyes, both Conditioners A and B have a very small effect on the wet combing work. This is due to the lack of reactive -SH groups on the surface of the fiber. When compared to stearalkonium chloride both Conditioners A and B were not very durable, but were more effective than stearalkonium chloride before shampooings.

Table III shows the utility of the better conditioner from Table II as a 5 minute treatment. It is obvious from this data that Conditioner B is very durable when compared to stearalkonium chloride.

Table IV demonstrates the versatility of several conditioners in waving lotions. All of the tested compounds reduce the wet combing work initially, with the disulfhydryl compound, Conditioner A, and Conditioner B being the most durable through 8 shampooing. These compounds were also more effective than the commercially available reactive protein conditioners [Kerasol (nonionic) and Croquat WKP (cationic) both available from Croda, Inc.].

The liquid retention of untreated hair is about 35% while for reduced and bleached hair the liquid retention is increased to 40-46% depending on the pH of the treatment. From the data in Table IV, it can be seen that the dithio conditioner greatly reduced the liquid retention, while the disulfhydryl compound had a much smaller effect. The remaining compounds slightly increased the liquid retention of the reduced hair.

The following non-limiting compounds illustrate typical compositions within the scope of this invention. In the examples Conditioner A and Conditioner B are as defined above.

EXAMPLE V

| Ingredient | Percent |
|---|---|
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Conditioner A | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |

EXAMPLE VI

| Ingredient | Percent |
|---|---|
| Water | 87.055 |
| Acetamide MEA | 3.000 |
| Hydrolyzed Animal Collagen | 0.700 |
| Glycol Stearate | 3.000 |
| Cetyl Alcohol | 1.300 |
| Conditioner B | 2.000 |
| Hydroxyethylcellulose | 0.850 |
| Polysorbate 20 | 1.000 |
| Hydrolyzed Keratin | 0.100 |
| Fragrance | 0.500 |
| Preservatives and Dyes | 0.495 |
| | 100.000 |

EXAMPLE VII

| Ingredient | Percent |
|---|---|
| Water | q.s. |
| Conditioner A | 3.500 |
| Benzyl Alcohol | 3.000 |
| Cetyl Alcohol | 0.500 |
| Hydroxyethylcellulose | 1.000 |
| Fragrance | 0.500 |
| Preservatives and Dyes | 0.500 |
| Sodium Citrate | 0.015-0.020 |
| Citric Acid | 0.015-0.020 |
| | 100.00 |

EXAMPLE VIII

| Ingredient | Percent |
|---|---|
| Water | q.s. |
| Conditioner B | 3.500 |
| Benzyl Alcohol | 3.000 |
| Cetyl Alcohol | 0.500 |
| Hydroxyethylcellulose | 1.000 |
| Fragrance | 0.500 |

-continued

| Ingredient | Percent |
|---|---|
| Preservatives and Dyes | 0.500 |
| Sodium Citrate | 0.015-0.020 |
| Citric Acid | 0.015-0.020 |
| | 100.000 |

Sodium citrate and citric acid are added to maintain buffer at pH 5.0.

What is claimed is:

1. Compounds useful as hair conditioners for human hair represented by the formulas:

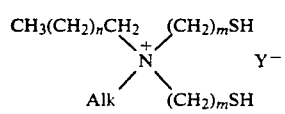

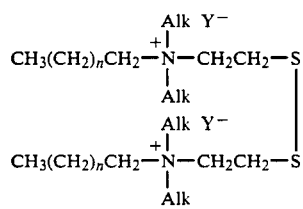

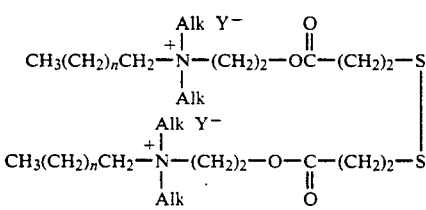

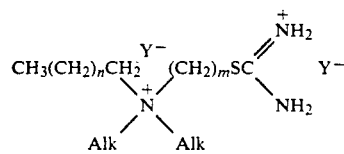

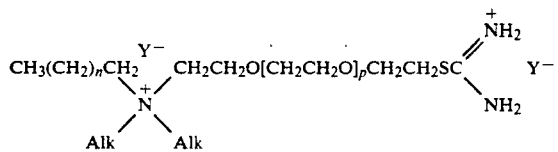

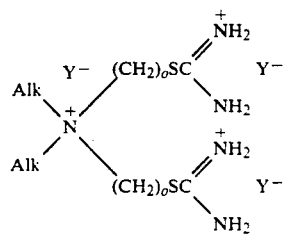

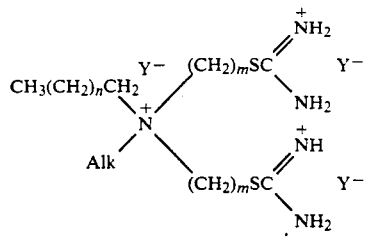

wherein
Alk is an alkyl group containing from about 1 to about 4 carbon atoms
Y is an anion
n is an integer with a value of from about 10 to 24
m is an integer with a value of from about 1 to about 4
o is an integer with a value of from about 8 to about 11
p is an integer with a value of from about 0 to 20
provided that, in compounds with only one n integer, the total number of carbon atoms in the cation is not greater than 28, and in compounds with two n integers, the total number of carbon atoms in the cation is not more than about 52, and further compounds in which one or both long chain alkyl groups is interrupted with a phenylene group so that the structure of the interrupted group can be represented by the formulas:

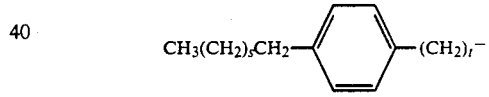

wherein s is an integer of from about 8 to about 17 and t is an integer from about 1 to about 5.

2. A compound of the formula:

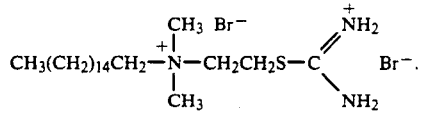

3. A compound of the formula:

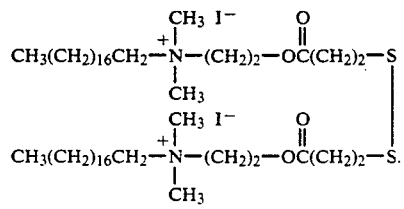

4. A compound of the formula:

5. A compound of the formula:
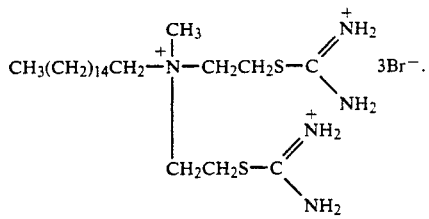
6. A compound of the formula:
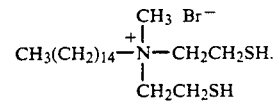
7. A compound of the formula:
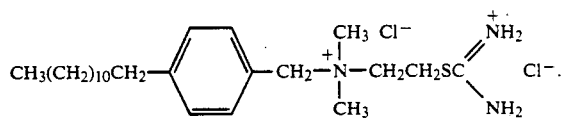
8. A compound of the formula:
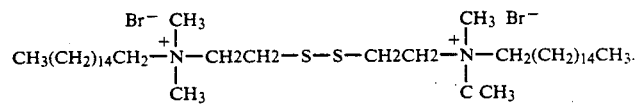
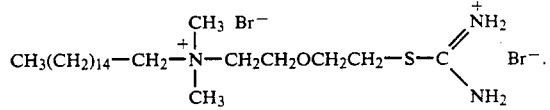
* * * * *